United States Patent [19]
Bruckner et al.

[11] Patent Number: 5,695,520
[45] Date of Patent: Dec. 9, 1997

[54] PRESSURE-APPLYING DEVICE HAVING PLATE-SUPPORTED PRESSURE-APPLYING BODY SECURED TO FLEXIBLE BAND

[76] Inventors: James V. Bruckner; Robert F. Gurnsey, both of P.O. Box 297, Clinton, Ark. 72031; Tony A. Bruckner, P.O. Box 907, Clinton, Ark. 72031

[21] Appl. No.: 567,281

[22] Filed: Dec. 5, 1995

[51] Int. Cl.[6] .................................................. A61B 17/00
[52] U.S. Cl. ..................................... 606/204; 606/201
[58] Field of Search ............................... 606/191–204, 606/1

[56] References Cited

U.S. PATENT DOCUMENTS

| | | |
|---|---|---|
| 4,243,028 | 1/1981 | Puyana . |
| 4,308,861 | 1/1982 | Kelly . |
| 4,323,232 | 4/1982 | Terpening . |
| 4,479,495 | 10/1984 | Isaacson . |
| 4,590,939 | 5/1986 | Sakowski . |
| 4,716,898 | 1/1988 | Chauve et al. . |
| 5,078,728 | 1/1992 | Giarratano . |
| 5,234,459 | 8/1993 | Lee . |
| 5,295,996 | 3/1994 | Blair . |
| 5,312,350 | 5/1994 | Jacobs . |
| 5,512,056 | 4/1996 | Stevens et al. ................ 606/203 |

FOREIGN PATENT DOCUMENTS

| | | | |
|---|---|---|---|
| 0462088 | 12/1991 | European Pat. Off. | ............... 606/201 |
| 267909 | 5/1989 | Germany . | |

*Primary Examiner*—Glenn Dawson
*Attorney, Agent, or Firm*—Flanagan & Flanagan

[57] ABSTRACT

A pressure-applying device for relieving distress includes a pressure applicator having a plate member and a pressure-applying body attached to and protruding from one of a pair of opposite surfaces of the plate member. The plate member has a central portion with a pair of opposite surfaces facing in opposite directions and a peripheral portion surrounding the central portion and having a pair of first opposite sides respectively connected to opposite ends of the central portion and a pair of second opposite sides spaced from a pair of opposite edges of the central portion so as to define respective elongated enclosed slots within the plate member between the second opposite sides of the peripheral portion and the pair of opposite edges of the central portion of the plate member. The device also includes a flexible strap attached to the plate member and adapted for wrapping and securing around a part of the body of a user so that the pressure-applying body is between the flexible strap and part of the body and is in contact with a selected point on the part of the body of the user for applying pressure thereto.

17 Claims, 2 Drawing Sheets

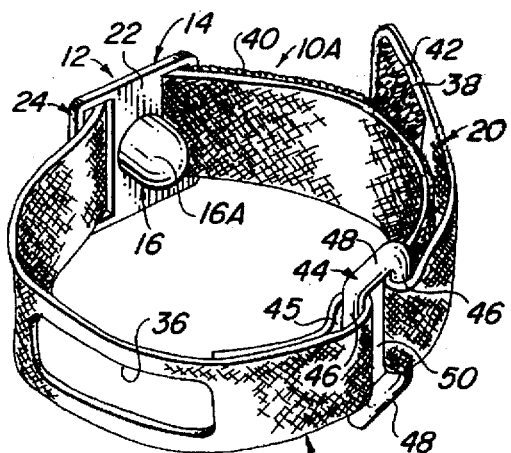
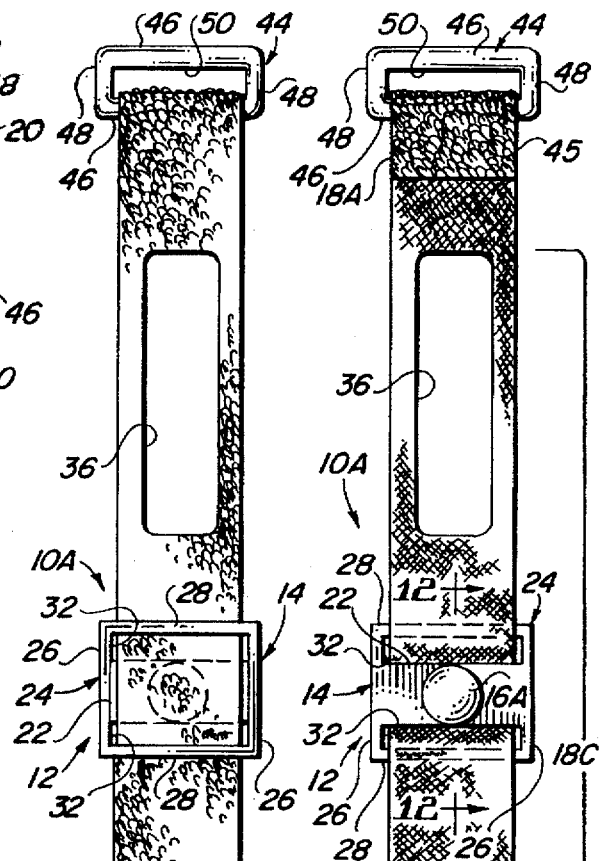
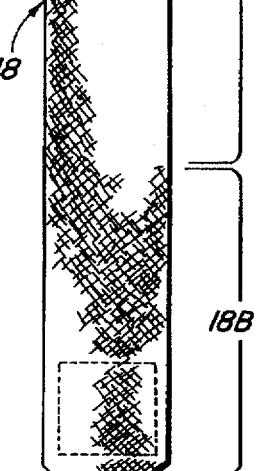
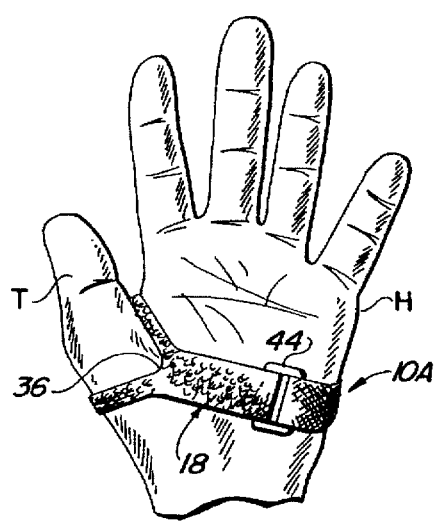
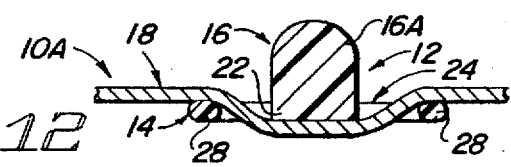
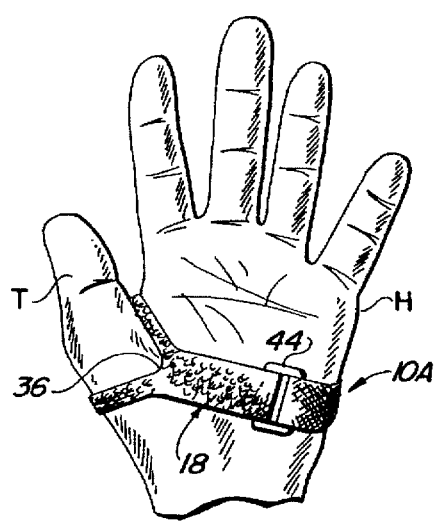

PRESSURE-APPLYING DEVICE HAVING PLATE-SUPPORTED PRESSURE-APPLYING BODY SECURED TO FLEXIBLE BAND

BACKGROUND OF THE INVENTION

1. Field of the Invention

The present invention generally relates to devices for applying pressure to selected points of the body and, more particularly, relates to a pressure-applying device employing a plate-supported pressure-applying body secured to a flexible band-like strap.

2. Description of the Prior Art

Many people at various times and for a variety of different reasons suffer from headaches and others from nausea induced by motion sickness which may lead to vomiting and/or other related physical distress. A variety of pressure-applying devices have been developed over the years to relieve these maladies. Other pressure-applying devices have been developed for use as tourniquets or for treating certain conditions or injuries or for improving the athletic performance of certain limbs of the human body. All of these devices generally function by applying pressure to selected points on the human or animal body.

Representative examples of the above pressure application devices are disclosed in U.S. Pat. Nos. 4,243,028 to Puyana, 4,308,861 to Kelly, 4,323,232 to Terpening, 4,479,495 to Isaacson, 4,590,939 to Sakowski, 4,716,898 to Chauve et al., 5,078,728 to Giarratano, 5,234,459 to Lee, 5,295,996 to Blair, 5,312,350 to Jacobs and German Pat. No. 267,909 to Glaubitt.

Common elements in most of these devices include a flexible strap with a fastening means and a protrusion attached to the inside of the strap for the application of pressure at a desired location on the body. The technique used is generally referred to as acupressure and is derived from the practice generally known as acupuncture, whereby the body is punctured with needles at key locations to cure disease or to relieve pain. In acupressure, however, relief is obtained not through puncturing the skin, but rather by the application of pressure to selected areas on the body.

Problems exist, however, with present acupressure devices. Most of the devices require a multiplicity of operations to assemble and thus are relatively expensive to produce. Also, many of the devices appear to inadequately support the pressure applying component. Consequently, a need still exists for an acupressure-type device which overcomes the aforementioned problems existing in the prior art.

SUMMARY OF THE INVENTION

The present invention provides a pressure-applying device designed to satisfy the aforementioned need. The pressure-applying device of the present invention basically employs a plate-supported pressure-applying body secured to an elongated flexible band-like strap. Such device is relatively simple to assemble and thus is relatively less expensive to produce than most prior art devices. Additionally, by attaching the pressure-applying body on a rigid plate member secured on the flexible strap, the pressure-applying body is supported in a more stable manner and thus is more effective in applying pressure to the desired point on the body.

Accordingly, the present invention is directed to a device for relieving distress by application of pressure. The pressure-applying device comprises: (a) a pressure applicator including (i) a plate member having a generally flat central portion with a pair of opposite surfaces facing in opposite directions and a peripheral portion surrounding the central portion and having a pair of first opposite sides respectively connected to opposite ends of the central portion and a pair of second opposite sides spaced from a pair of opposite edges of the central portion so as to respectively define elongated enclosed slots within the plate member between the pair of second opposite sides of the peripheral portion and the pair of opposite edges of the central portion of the plate member, and (ii) a pressure-applying body attached on and protruding outwardly from one of the opposite surfaces of the central portion of the plate member in one of the opposite directions; (b) an elongated flexible strap extending through the pair of slots of the plate member and adapted to be wrapped around a part of a body of a user such that the pressure-applying body on the plate member is positioned between the central portion thereof and a selected point on the part of the body of the user for making contact therewith and applying pressure thereto; and (c) fastening means on the elongated flexible strap for releasably securing the strap wrapped around the part of the body of the user. The enclosed slots in the plate member extend substantially parallel to each other and have lengthwise dimensions extending in a generally transverse relationship to the lengthwise dimension of the flexible strap. The flexible strap has a pair of opposite end portions with the middle portion located and connected therebetween.

In a first embodiment of the pressure-applying device, the opposite end portions of the flexible strap are inserted through the respective enclosed slots of the plate member and secured about the second opposite sides of the peripheral portion thereof adjacent to the enclosed slots. More particularly, one opposite end portion of the flexible strap extends through one enclosed slot and is doubled back on and fixedly attached to itself to form a fixed loop securing the one end portion of the flexible strap to one of the second opposite sides of the peripheral portion of the plate member. The other opposite end portion of the flexible strap is a free end inserted through the other enclosed slot and and doubled back on and releasably attached to itself to releasably secure the other opposite end portion of the flexible strap to the other of the second opposite sides of the peripheral portion of the plate member.

In a second embodiment of the pressure-applying device, an elongated middle portion of the flexible strap is inserted through the enclosed slots and extends along and over the other of the opposite surfaces of the central portion of the plate member. Preferably, the plate member and central and peripheral portions thereof having substantially rectangular configuration. Also, an elongated opening is formed in the flexible strap in the middle portion thereof adjacent to one of the opposite end portions thereof for receiving therethrough the thumb of the user.

In the first embodiment of the pressure-applying device, the fastening means includes a pair of complementary pluralities of mateable hook and loop fastening elements. One plurality of the fastening elements is attached at least to the free end of the other opposite end portion of the flexible strap and the other plurality of fastening elements is attached at least to the middle portion of the flexible strap for engagement with the one plurality of fastening elements upon the doubling back of the other opposite end portion of the flexible strap after insertion of the free end through the respective enclosed slot of the plate member.

In the second embodiment of the pressure-applying device, the fastening means is the same as described above with respect to the first embodiment and in addition thereto, the fastening means also includes an eyelet member. The one end portion of the flexible strap extends through the eyelet member and is doubled back on and fixedly attached to itself to form a fixed loop securing the flexible strap to the eyelet member. The eyelet member preferably is of a rectangular configuration having a pair of transverse side portions and a pair of lateral end portions extending between and rigidly interconnecting the transverse side portions so as to define an enclosed eye through the eyelet member receiving the flexible strap therethrough.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 9 is a perspective view of a second embodiment of the pressure-applying device of the present invention being shown in a fastened condition.

FIG. 10 is an outside plan view of the device of FIG. 9 being shown in an unfastened condition.

FIG. 11 is an inside plan view of the device of FIG. 9 being shown in an unfastened condition.

FIG. 12 is an enlarged fragmentary cross-sectional view of the plate member and pressure-applying body of the device taken along line 12—12 of FIG. 11.

FIG. 13 is a palm down view of the device of FIG. 9 applied on a user's hand.

FIG. 14 is a palm up view of the device of FIG. 9 applied on the user's hand.

DETAILED DESCRIPTION OF THE INVENTION

Figure 5:
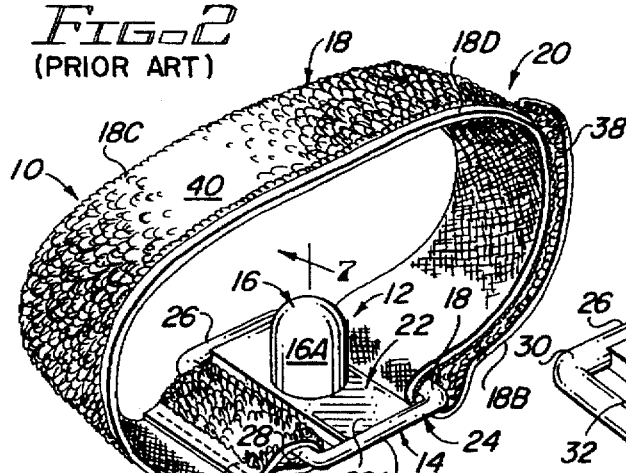
FIG. 5 is a perspective view of a first embodiment of the pressure-applying device of the present invention being shown in a fastened condition.
Figure 6:
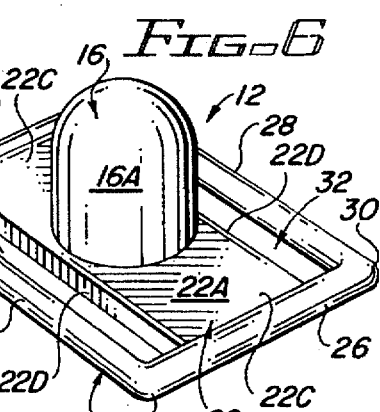
FIG. 6 is an enlarged perspective view of a plate member and a pressure-applying body of the device being shown removed from a flexible strap of the device.
Figure 7:
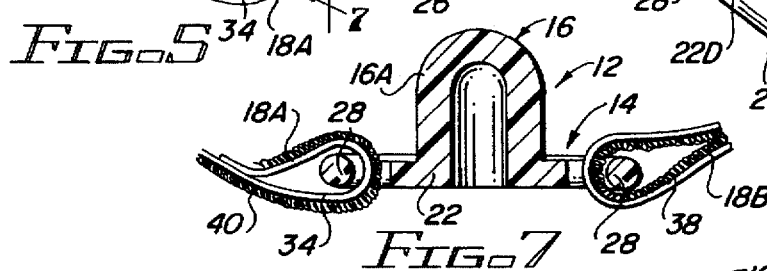
FIG. 7 is an enlarged fragmentary cross-sectional view of the plate member and pressure-applying body of the device taken along line 7—7 of FIG. 5.
Figure 8:
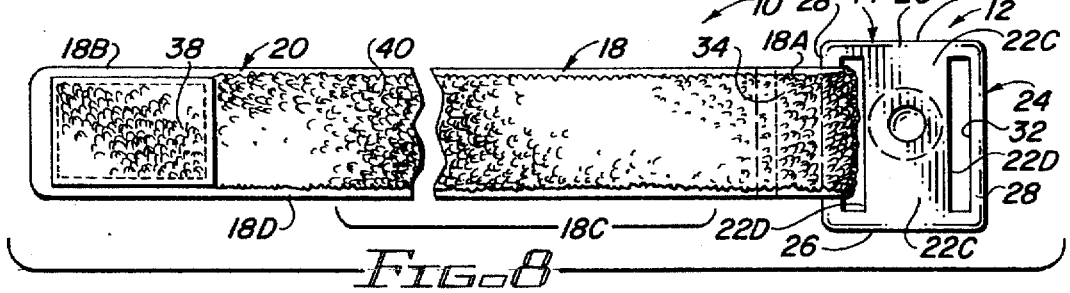
FIG. 8 is a foreshortened outside plan view of the flexible strap and plate member of the device being shown in an unfastened condition.

Referring to the drawings and particularly to FIGS. 5 to 8, there is illustrated a first embodiment of a pressure-applying device of the present invention, being generally designated 10, for wrapping around and applying pressure at a selected point on a part of the body, such the wrist, of a user so as to help relieve pain, such as nausea associated with motion sickness. In FIGS. 9-14, there is illustrated a second embodiment of the pressure-applying device of the present invention, being generally designated 10A, for wrapping around and applying pressure at another selected point on another part of the body, such as the backside B of the hand H, of the user so as to help relieve pain, such as from a headache.

Basically, in both first and second embodiments, the pressure-applying device 10, 10A comprises a pressure applicator 12 which includes a plate member 14 and a pressure-applying body 16 attached to and protruding from one side of the plate member 14. The pressure-applying device 10, 10A also includes an elongated flexible strap 18 attached to the plate member 14 and adapted for wrapping around the respective part of the body of the user to position the plate member 14 such that the pressure-applying body 16 is between the plate member 14 and respective part of the user's body and in contact with a selected point thereon. Finally, the pressure-applying device 10, 10A includes fastening means 20 for releasably securing the flexible strap 18 wrapped in the desired manner about the part of the user's body.

More particularly, the plate member 14 of the pressure applicator 12 is preferably made of a substantially rigid material, such as a suitable injection molded plastic, and is substantially rectangular in shape having a length which is slightly greater than the width. The plate member 14 has a generally flat central portion 22 with a pair of opposite surfaces 22A, 22B facing in opposite directions and a peripheral portion 24 which surrounds the central portion 22. Preferably, the plate member 14 and the central portion 22 and peripheral portion 24 thereof have substantially rectangular configurations. The peripheral portion 24 has a pair of first opposite sides 26 and a pair of second opposite sides 28 extending between and rigidly, and preferably integrally, interconnecting the first opposite sides 26 at the respective opposite ends thereof to define four corners 30 of the peripheral portion 24. The pair of first opposite sides 26 of the peripheral portion 24 respectively connected to the pair of opposite ends 22C of the central portion 22, whereas the pair of second opposite sides 28 are spaced from a pair of opposite edges 22D of the central portion 22 so as to respectively define a pair of elongated enclosed slots 32 within the plate member 14 between the pair of second opposite sides 28 of the peripheral portion 24 and the pair of opposite edges 22C of the central portion 22. Each slot 18 is arranged in generally parallel relationship to one another on the plate member 12 and is defined by interconnected pairs of spaced interior long and short edges 18A and 18B defined in the plate member 12.

Also, the pressure-applying body 16 of the pressure applicator 12 has an exterior curvilinear surface 16A and is attached, preferably integrally, with the inner one of the opposite surfaces 22A of the central portion 22 of the plate member 14 in the corresponding one of the opposite directions therefrom. The pressure applying body 14 is preferably made of a substantially rigid material and protrudes outwardly from the inner surface 22A of the central portion 22 between the pair of enclosed slots 32 of the plate member 14. The body 14 may be fabricated into different sizes and shapes depending upon the needs of the user.

The flexible strap 18 of the pressure-applying device 10, 10A is preferably made of an inelastic material, such as a suitable plastic, is substantially rectangular in shape, and has a pair of opposite surfaces 18D, 18E. The flexible strap 18 also includes a pair of opposite end portions 18A, 18B and an elongated middle portion 18C located and extending between and connected with the opposite end portions 18A, 18B. The middle portion 18C is substantially greater in length than each of the pair of opposite end portions 18A, 18B. The respective enclosed slots 32 in the plate member 14 have lengths much shorter than and extending in a generally transverse relationship to the length of the flexible strap 18.

In the first embodiment of the pressure-applying device 10 shown in FIGS. 5–8, the opposite end portions 18A, 18B of the flexible strap 18 are inserted through the respective enclosed slots 32 of the plate member 14 and secured about the second opposite sides 28 of the peripheral portion 24 thereof adjacent to the enclosed slots 32. More particularly, one opposite end portion 18A of the flexible strap 18 extends through one enclosed slot 32 and is doubled back on and fixedly attached to itself to form a fixed loop 34 securing the one end opposite portion 18A of the flexible strap 18 to one second opposite side 28 of the peripheral portion 24. The other opposite end portion 18B of the flexible strap 18 is a free end inserted through the other enclosed slot 32 and and doubled back on and releasably attached to itself to releasably secure the other opposite end portion 18B of the flexible strap 18 to the other of the second opposite sides 28 of the peripheral portion 24 of the plate member 14.

In the second embodiment of the pressure-applying device 10A shown in FIGS. 9–14, the elongated middle portion 18C of the flexible strap 18 is inserted through the enclosed slots 32 and extends along and over the outer opposite surface 22B of the central portion 22 of the plate member 14. Also, in the second embodiment only, an elongated opening 36 is formed in the flexible strap 18 in the middle portion 18C thereof adjacent to the one opposite end portion 18A thereof for receiving therethrough the thumb T of the user, as shown in FIGS. 13 and 14. The pressure is applied by the device 10A to the backside of the hand H in FIGS. 13 and 14, whereas in the device 10 of FIGS. 5–8, the pressure is applied to the inside of the wrist.

In both first and second embodiments of the pressure-applying device 10, 10A, the fastening means 20 includes a pair of complementary pluralities of mateable hook and loop fastening elements 38, 40 disposed on the outer side 18D of the flexible strap 18. Preferably, although not necessarily, the hook fastening elements 38 are attached to and extend along the free end of the other opposite end portion 18B of the flexible strap 18, whereas the loop fastening elements 40 are attached at least to the middle portion 18C of the flexible strap 18 for engagement with the hook fastening elements 38 upon the doubling back of the other opposite end portion 18B of the flexible strap 18 after insertion of the free end through the respective enclosed slot 32 of the plate member 14. Preferably, the hook fastening elements 38 are disposed on a patch 42 of material secured on the outer side 18D of the flexible strap 18, whereas the loop fastening elements 40 are disposed and mounted directly on the outer side 18D of the flexible strap 18. The loop fastening elements 40 cover a much greater area of the outer side 18D of the flexible strap 18 than that covered by the hook fastening elements 38 on the patch 42 of material. Thus, the location of attachment of the hook fastening elements 38 to the loop fastening elements 40 on the flexible strap 18 can be varied for wrapping the flexible strap 18 about parts of the body of the user having different sizes. The loop fastening elements 40 are attached to and covers substantially the entire area of the outer side 18D of the flexible strap 18.

In the second embodiment of the pressure-applying device, the fastening means 20 is the same as described above with respect to the first embodiment and in addition thereto, the fastening means 20 also includes an eyelet member 44. The one opposite end portion 18A of the flexible strap 18 extends through the eyelet member 44 and is doubled back on and fixedly attached to itself to form a fixed loop 45 securing the flexible strap 18 to the eyelet member 44. More particularly, the eyelet member 44 preferably has a rectangular configuration formed by a pair of transverse side portions 46 and a pair of lateral end portions 48 extending between and rigidly interconnecting the transverse side portions 46 so as to define an enclosed eye 50 through the eyelet member 44 receiving the flexible strap 18 therethrough.

The first embodiment of the device 10 is relatively easy to correctly place around the user's wrist and thus needs no explanation other than merely place the body 16 at the point on the inside of the wrist where a person's pulse is usually taken. However, a short explanation would be very useful as to how to find the pressure point and to place the second embodiment of the device 10A on the user's hand H. First, flatten the hand H and move the thumb up tight against the side of the hand. This action will create a hump on the hand next to the thumb. Locate a position in the center of this hump. The headache relieving pressure point is located directly below this position. Next, place the thumb through the opening 36 in the flexible strap 18 with the fastening eyelet member 44 in the palm of the hand and the pressure-applying body 16 on the backside of the hand. Lace the free end of the flexible strap 18 through the eye 50 of the eyelet member 44 and cinch it medium tight, locking the free end member down by depressing the hook elements 38 into the loop elements 40. Now, slide the pressure-applying body 16 along the strap 18 until it is located at and depresses the pressure point adjacent to the thumb T. Press down and rock the body 16 back and forth. A slight twinge will be felt, confirming the proper location. Adjust the tightness as required.

Figure 1:
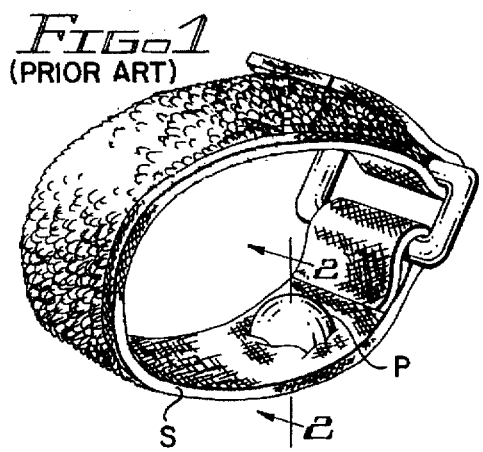
FIG. 1 is a perspective view of a first example of a prior art pressure-applying device having a pressure-applying body embedded in a flexible strap being shown in a fastened condition.
Figure 3:
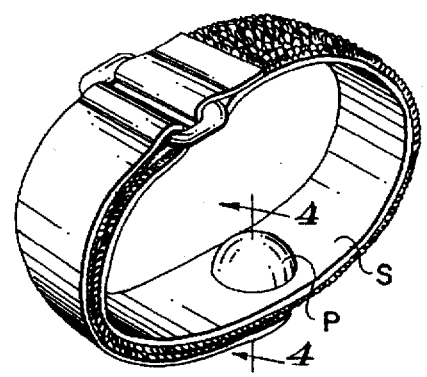
FIG. 3 is a perspective view of a second example of a prior art pressure-applying device being shown in a fastened condition.
Figure 2:
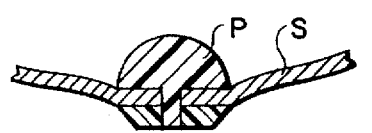
FIG. 2 is an enlarged fragmentary cross-sectional view of the first prior art device taken along line 2—2 in FIG. 1.
Figure 4:
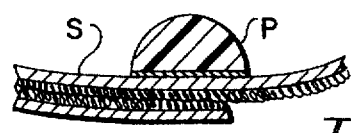
FIG. 4 is an enlarged fragmentary cross-sectional view of the second prior art device taken along line 4—4 of FIG. 3.

In summary, the problems inherent in the prior art devices shown in FIGS. 1 to 4 where the pressure applying body P is embedded in the flexible strap S are overcome by use of the pressure applying device 10, 10A of the present invention wherein the pressure applying body 16 is not so embedded on the flexible strap 18 but rather is attached to the plate member 14 which connects each of the ends of the strap 18 wrapped around the wrist of the user. This use of the pressure applying body 16 mounted on the plate member 14 simplifies assembly, decreases the cost of production and increases the overall durability of the device 10, 10A.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

I claim:

1. A device for relieving distress by application of pressure, said device comprising:
   (a) a pressure applicator including
      (i) a plate member having a central portion with a pair of opposite surfaces facing in opposite directions and a peripheral portion surrounding said central portion and having a pair of first opposite sides respectively connected to opposite ends of said central portion and a pair of second opposite sides spaced from a pair of opposite edges of said central portion so as to respectively define elongated enclosed slots within said plate member between said pair of second opposite sides of said peripheral portion and said pair of opposite edges of said central portion of said plate member, and (ii) a pressure-applying body attached on and protruding outwardly from one of said opposite surfaces of said central portion of said plate member in one of said opposite directions;

(b) an elongated flexible strap extending through said pair of slots of said plate member and adapted to be wrapped around a part of a body of a user such that said pressure-applying body on said plate member is positioned between said central portion thereof and a selected point on the part of the body of the user for making contact therewith and applying pressure thereto; and (c) fastening means on said flexible strap for releasably securing said strap wrapped around the part of the body of the user;

(d) said flexible strap having a pair of opposite end portions, and elongated middle portion located and connected therebetween and an elongated opening formed in said middle portion of said flexible strap adjacent to one of said opposite end portions thereof for receiving therethrough a thumb of the user.

2. The device of claim 1 wherein said plate member has a substantially rectangular configuration.

3. The device of claim 2 wherein said central portion of said plate member has a substantially rectangular configuration.

4. The device of claim 1 wherein said pressure-applying body of said pressure applicator has an exterior curvilinear surface.

5. The device of claim 1 wherein said pressure-applying body is integrally connected to said central portion of said plate member.

6. The device of claim 1 wherein said opposite end portions of said flexible strap are inserted through respective ones of said enclosed slots of said plate member and secured about said second opposite sides of said peripheral portion adjacent to said enclosed slots.

7. The device of claim 1 wherein one of said opposite end portions of said flexible strap extends through one of said enclosed slots and is doubled back on and fixedly attached to itself to form a fixed loop securing said one end portion of said flexible strap to one of said second opposite sides of said peripheral portion of said plate member.

8. The device of claim 7 wherein the other of said opposite end portions of said flexible strap is a free end inserted through the other of said enclosed slots and doubled back on and releasably attached to itself to releasably secure said other opposite end portion of said flexible strap to the other of said second opposite sides of said peripheral portion of said plate member.

9. The device of claim 1 wherein said elongated middle portion of said flexible strap is inserted through said enclosed slots and extends along and over the other of said opposite surfaces of said central portion of said plate member.

10. The device of claim 1 wherein said fastening means includes a pair of complementary pluralities of mateable hook and loop fastening elements.

11. The device of claim 10 wherein one of said fastening elements is disposed on an outer side of said flexible strap and attached at least to a free end of said other opposite end portion of said flexible strap and the other of said fastening elements is disposed on said outer side of said flexible strap and attached at least to said middle portion of said flexible strap for engagement with said one of said fastening elements upon the doubling back of said other opposite end portion of said flexible strap after insertion through said respective enclosed slot of said plate member.

12. The device of claim 10 wherein said fastening means also includes an eyelet member having a pair of transverse side portions and a pair of lateral end portions extending between and rigidly interconnecting said transverse side portions so as to define an enclosed eye through said eyelet member for receiving said flexible strap therethrough.

13. The device of claim 12 wherein one end portion of said flexible strap extends through said eye of said eyelet member and is doubled back on and fixedly attached to itself to form a fixed loop securing said flexible strap to said eyelet member.

14. The device of claim 10 wherein one of said fastening elements is disposed on a patch of material secured on said outer side of said flexible strap and the other of said fastening elements is disposed directly on said outer side of said flexible strap, said other of said fastening elements covering a greater area of said outer side of said flexible strap than covered by said one of said fastening elements on said patch of material such that the location of attachment of said one of said fastening elements to said other of fastening elements on said flexible strap can be varied for wrapping said flexible strap about parts of the body of the user having different sizes.

15. The device of claim 14 wherein said other of said fastening elements is attached to and covers substantially the entire area of said outer side of said flexible strap.

16. The device of claim 1 wherein said enclosed slots in said plate member have lengthwise dimensions extending in a generally transverse relationship to a lengthwise dimension of said flexible strap.

17. The device of claim 1 wherein said enclosed slots in said plate member extend in substantially parallel relationship to one another.

* * * * *